United States Patent [19]

Hudlicky

[11] Patent Number: 5,306,846
[45] Date of Patent: Apr. 26, 1994

[54] SYNTHESIS OF CYCLITOLS FROM SUBSTITUTED ARENE DIOLS

[75] Inventor: Thomas Hudlicky, Blacksburg, Va.

[73] Assignee: Virginia Tech Intellectual Properties, Blacksburg, Va.

[21] Appl. No.: 802,783

[22] Filed: Dec. 6, 1991

Related U.S. Application Data

[63] Continuation-in-part of Ser. No. 636,396, Dec. 31, 1990, abandoned, which is a continuation-in-part of Ser. No. 509,341, Apr. 16, 1990, abandoned.

[51] Int. Cl.$^5$ ............................................. C07C 35/08
[52] U.S. Cl. ................................. 568/832; 568/811; 568/822
[58] Field of Search ............... 568/834, 833, 832, 823, 568/822

[56] References Cited

U.S. PATENT DOCUMENTS

| | | | |
|---|---|---|---|
| 2,112,553 | 3/1938 | Barlow | 568/833 |
| 4,740,638 | 4/1988 | Taylor et al. | 568/832 |
| 4,988,682 | 1/1991 | Koaikowski | 568/833 |

FOREIGN PATENT DOCUMENTS 313426  5/1972  U.S.S.R. ............................ 568/833

OTHER PUBLICATIONS

McCasland et al., "J. Amer. Che. Soc." vol. 76, (1954) pp. 2373-2379.
Andersen et al., "J. Amer. Chem. Soc." vol. 79, (1957) pp. 1171-1174.

Primary Examiner—Werren B. Lone
Attorney, Agent, or Firm—Margaret A. Horn

[57] ABSTRACT

There are disclosed novel processes for the synthesis of novel intermediates useful in the of further synthesis of cyclitols and derivatives thereof.

26 Claims, 5 Drawing Sheets

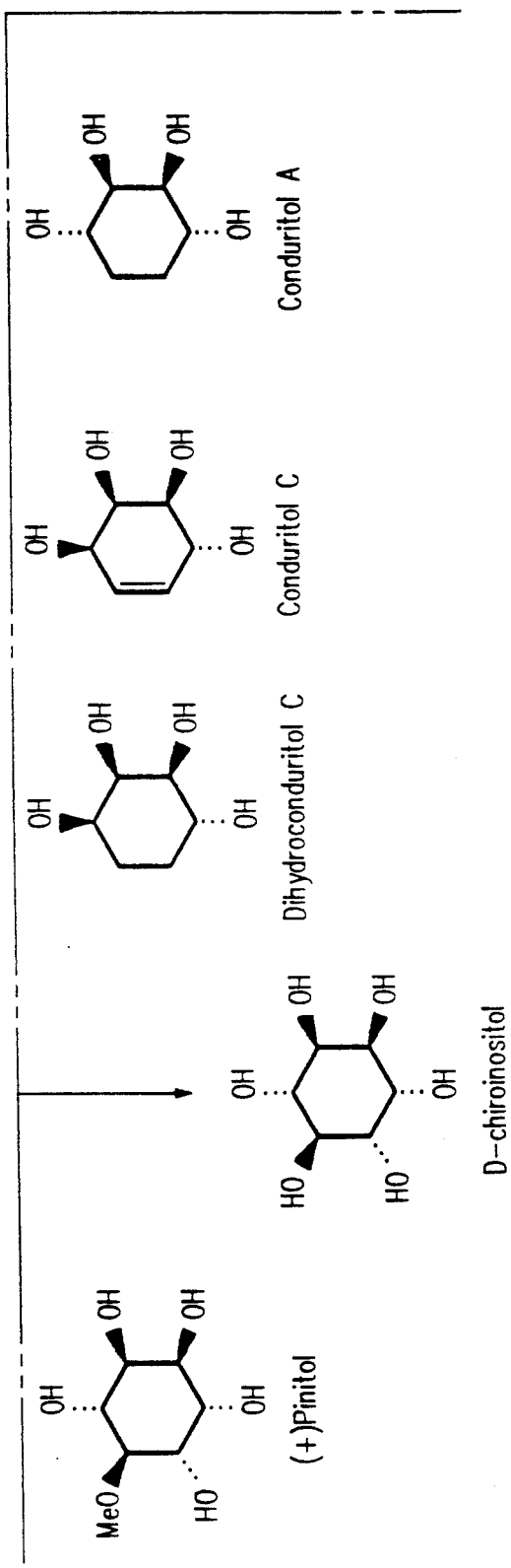
FIG. 1C
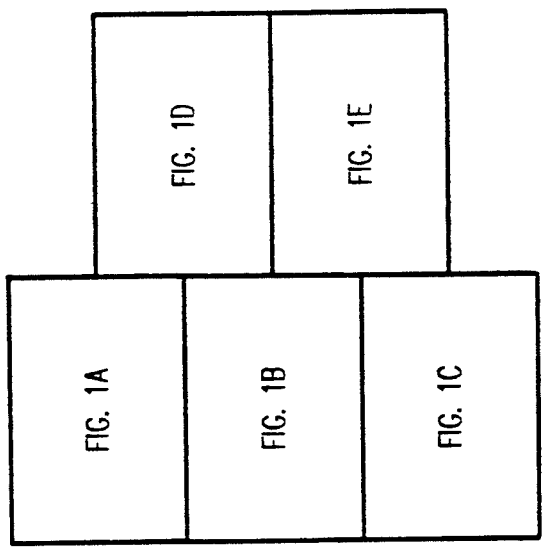
KEY TO FIG. 1

SYNTHESIS OF CYCLITOLS FROM SUBSTITUTED ARENE DIOLS

This application is a continuation-in-part of U.S. application Ser. No. 07/636,396, filed Dec. 31, 1990 (abandoned) which is a continuation-in-part of U.S. application Ser. No. 07/509,341, filed Apr. 16, 1990 (abandoned). This application is related to U.S. application Ser. No. 07/480,891, filed Feb. 16, 1990, now abandoned in favor of continuation in part application Ser. No. 07/802/943, filed Dec. 6, 1991.

BACKGROUND OF THE INVENTION

The present invention relates to the synthesis of cyclitols and derivatives thereof from substituted arene diols.

Cyclitols are polyoxyfunctional (i.e., having 2 to 6 hydroxy, alkoxy, aryloxy or phosphate functionalities) cyclohexane derivatives, and as such are classified as carbohydrates [Anderson, In *The Carbohydrates Chemistry and Biochemistry*, Pigman et al., Eds., Academic Pres: New York, Vol. la, Chap. 15, 1972]. All possible stereoisomers of these compounds are known to occur in nature (seven meso forms and one DL pair). Indeed, cyclitols appear to be present, both free and combined, in the tissues of nearly all living species [Posternak, T. *The Cyclitols*, Hermann: Paris, 1962]. Dihydroconduritols are a subclass of inositols in which the number of hydroxyl groups present is reduced to four. These compounds, along with conduritols (cyclohexenetetrols) are of interest because of their potential use as inhibitors for glycosidases [Postermak, T. *The Cyclitols*, Hermann: Paris, 1962].

Previous syntheses of these types of compounds have started from achiral sources and have either involved numerous steps, incomplete stereospecificity at some point, or did not lead to optically pure products [Posternak et al., Helv. Chim. Acta 36:251. 1953; Gorin, Can. J. Chem. 42:1749, 1964; Nakajima et al., S. Ber. 92:173, 1959]. Benzene-cis-diol has been used in a number of natural product syntheses [Carless et al., Tetrahedron Lett. 30:3113, 1989; Carless et al., Tetrahedron Lett. 30:1719, 1989]. Ley et al used the benzene diol to synthesize (+)-pinitol [Tetrahedron Letters 45:3463, 1989] and myo-inositol triphosphate [Tetrahedron Letters 29:5305, 1988]. One obvious disadvantage to using benzene-cis-diol in natural product synthesis, however, is the preclusion of enantiocontrolled synthesis without further (usually enzymatic) manipulations of the meso intermediates. For this and other reasons, the methods of the present invention utilize optically pure chiral synthons resulting from microbial oxidation of monosubstituted benzene derivatives.

Other syntheses of cyclitols are disclosed in Balci, M. et al., Tetrahedron 1990, 46, 3715; Secen et al., Tetrahedron Lett. 31:1323, 1990; Akbulut et al., J. Org. Chem. 53:3338, 1988; Sutbeyaz et al., J. Chem. Soc. Commun. 1330, 1988; Bruce et al., Tetrahedron Lett. 30:7257, 1989; Kobayashi et al., J. Org. Chem. 55:1169, 1990; and Gorin, Canadian J. Chem. 42:1748, 1964.

In 1970 Gibson and co-workers reported the enantioselective oxidation of toluene to cis-toluenediol [(+)-cis-2,3-dihydroxymethylcyclohexa-4,6-diene] by a mutant of Pseudomonas putida, a soil bacterium [Gibson et al., J. Biochemistry 9:1626 (1970)]. Since that time many other simple arenes were shown to yield diols of this type through microbial oxidation techniques [Jerina et al., Arch. Biochem. Biophys. 142:394 (1971); Gibson et al., Biochemistry 7:3795 (1968); Jeffrey et al., Biochemistry 14:575 (1975); Burlingame et al., J. Bacteriol. 168:55 (1986); Gibson et al., Biochem. Biophys. Res. Commun. 50:211 (1973); Gibson et al., J. Bacteriol. 119:930 (1974); Whited et al., J. Bacteriol. 166:1028 (1986); Ziffer et al., Tetrahedron 33:2491 (1977)].

Despite the operational simplicity and complete stereospecificity of the reaction producing such diols, little use of this transformation has been made in organic synthesis, save for a few recent reports. Hudlicky et al [J. Am. Chem. Soc. 110:4735 (1988)] used the toluene diol to synthesize enones useful for prostaglandin synthesis, aldehydes which are potential synthons for perhydroazulene terpenes, and cyclohexene oxide which is the descarbobenzoxy derivative of crotepoxide. Hudlicky et al [J. Org. Chem. 54:4239 (1989)] have also used the styrene diol to synthesize zeylena, another cyclohexene oxide. However, the full potential of such diols for synthesis of chiral synthons has not yet been fully realized.

SUMMARY OF THE INVENTION

The present invention takes advantage of the chirality introduced in the microbial oxidation of arene diols to simply and efficiently produce cyclitols. A short enantioselective approach to cyclitols is disclosed. The key to this synthetic approach is the use of substituted chiral arene diols. With such substituted diols, the molecule can be suitably modified to allow for face selectivity in subsequent hydroxylation sequences of oxygenation methods. Each subsequent stereocenter is fully controlled by that previously established. Almost any atom or functional group can therefore by placed in the periphery of the cyclohexane ring (OH, OR[R=alkyl or aryl], Cl, F, Br, I, $NH_2$, $N_3$, $NR_2$ NRH, etc.) Thus, surprisingly, a chiral cyclitol can be obtained from an achiral aromatic source.

The methods of the present invention are relatively simple and more economical than prior methods for such syntheses. A further advantage is provided by such methods in that cyclitols can be produced from C1 substituted arenes (such as halobenzenes, particularly chlorobenzene, toluene, styrene) which are often considered to be by-products. Thus, waste can be converted into useful sugars in accordance with the present invention. These and other advantages of the present invention will be apparent to those skilled in the art from the disclosure herein.

DESCRIPTION OF THE FIGURES

FIGS. 1A-1E show generalized scheme for control of stereochemistry in synthesis of cyclitols from chiral arene diols.

DETAILED DESCRIPTION OF THE INVENTION

Cyclitols can be synthesized in accordance with the present invention from appropriately substituted chiral arene diols. Arene diols of the general formula (I):

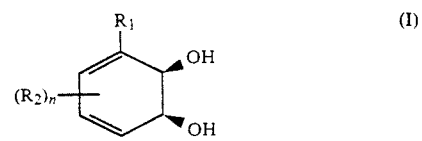

can be used in the methods of the present invention. $R_1$ can be a halogen (particularly chloro and bromo), lower alkyl (C1-C6 and preferably C1) or lower alkenyl (C1-C6 and preferably C1). $R_2$ is halogen or hydrogen where n is from 0 to 3. Preferably, $R_1$ is chloro and n is 0 such that the substituted arene is chlorobenzene.

The nature of various R groups will depend upon the desired cyclitol product as will be understood by those skilled in the art. Since the arene diols are synthesized by microbial oxidation, substitution of the arene diol is limited only by the microbial process (i.e., by the substituted arenes which can serve as a substrate for the microbial process).

Figure 1A:
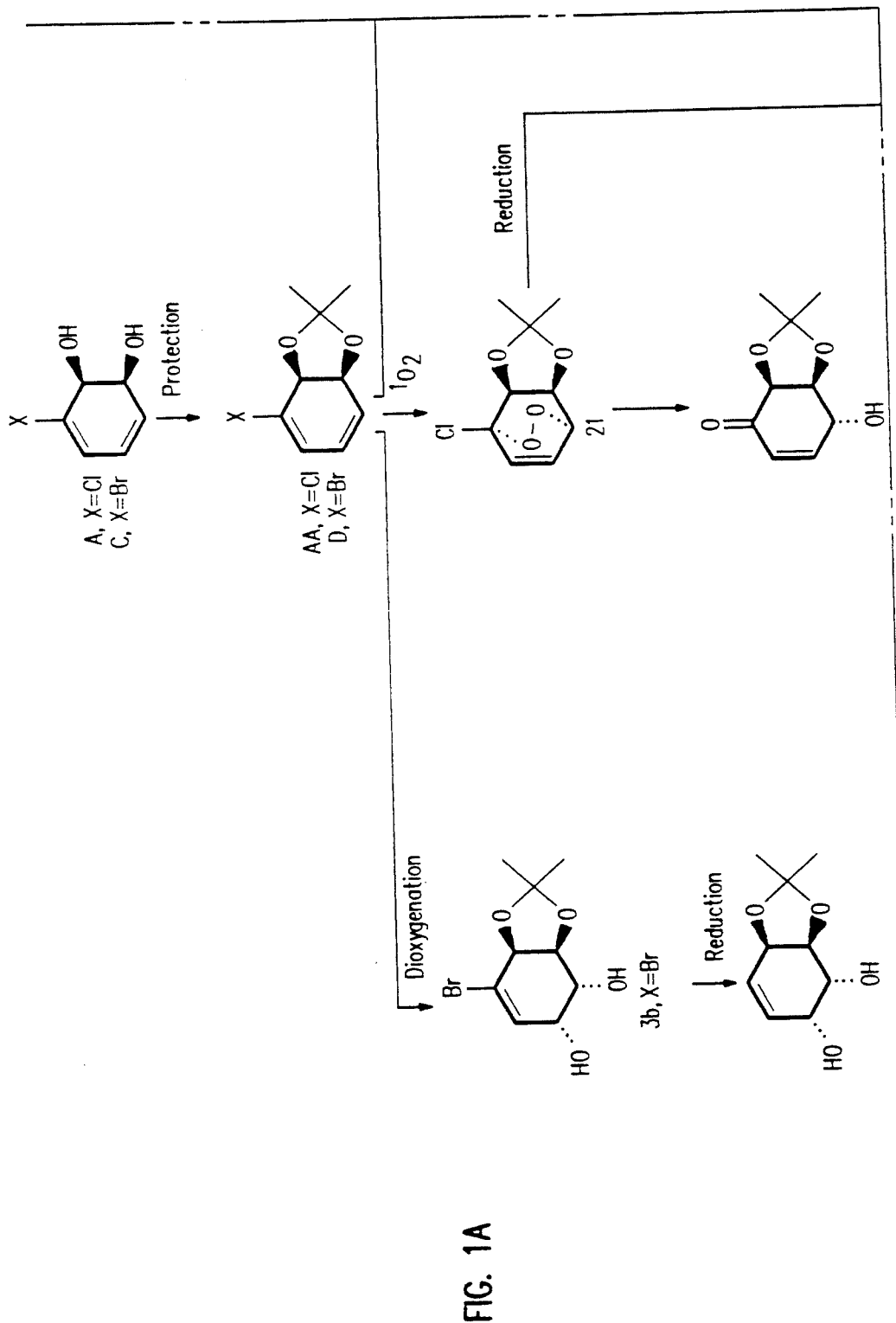
Figure 1B:
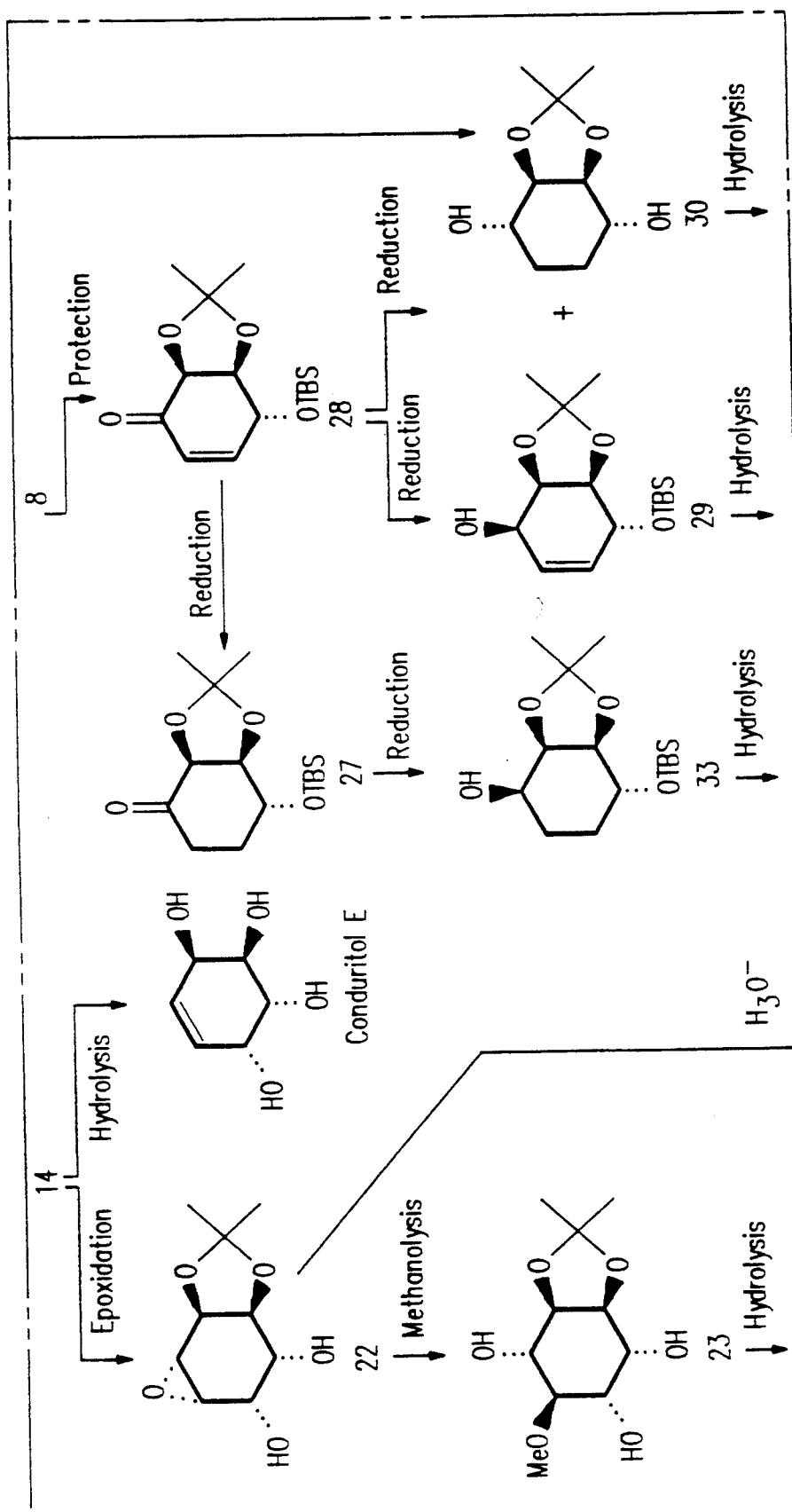
Figure 1D:
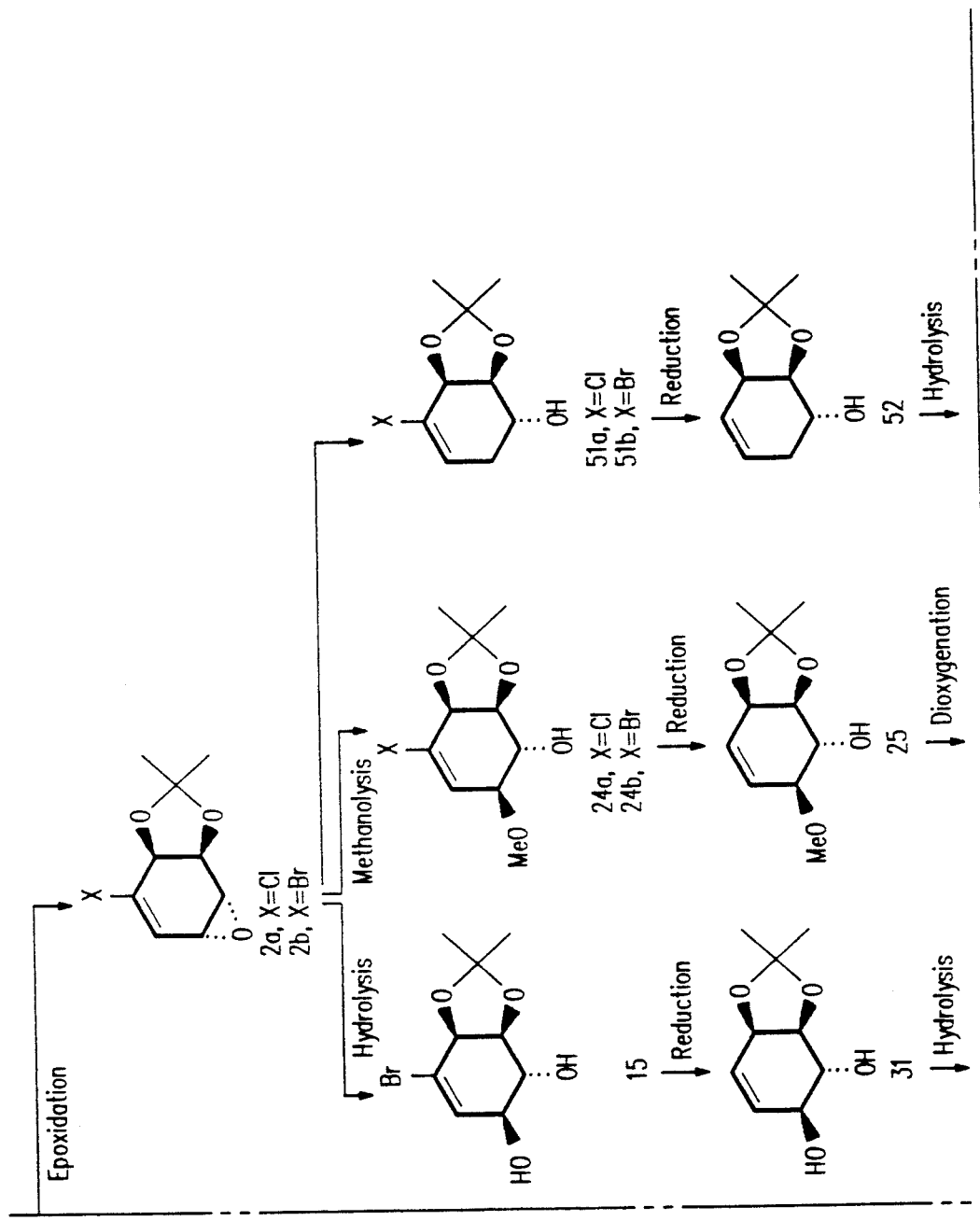
Figure 1E:
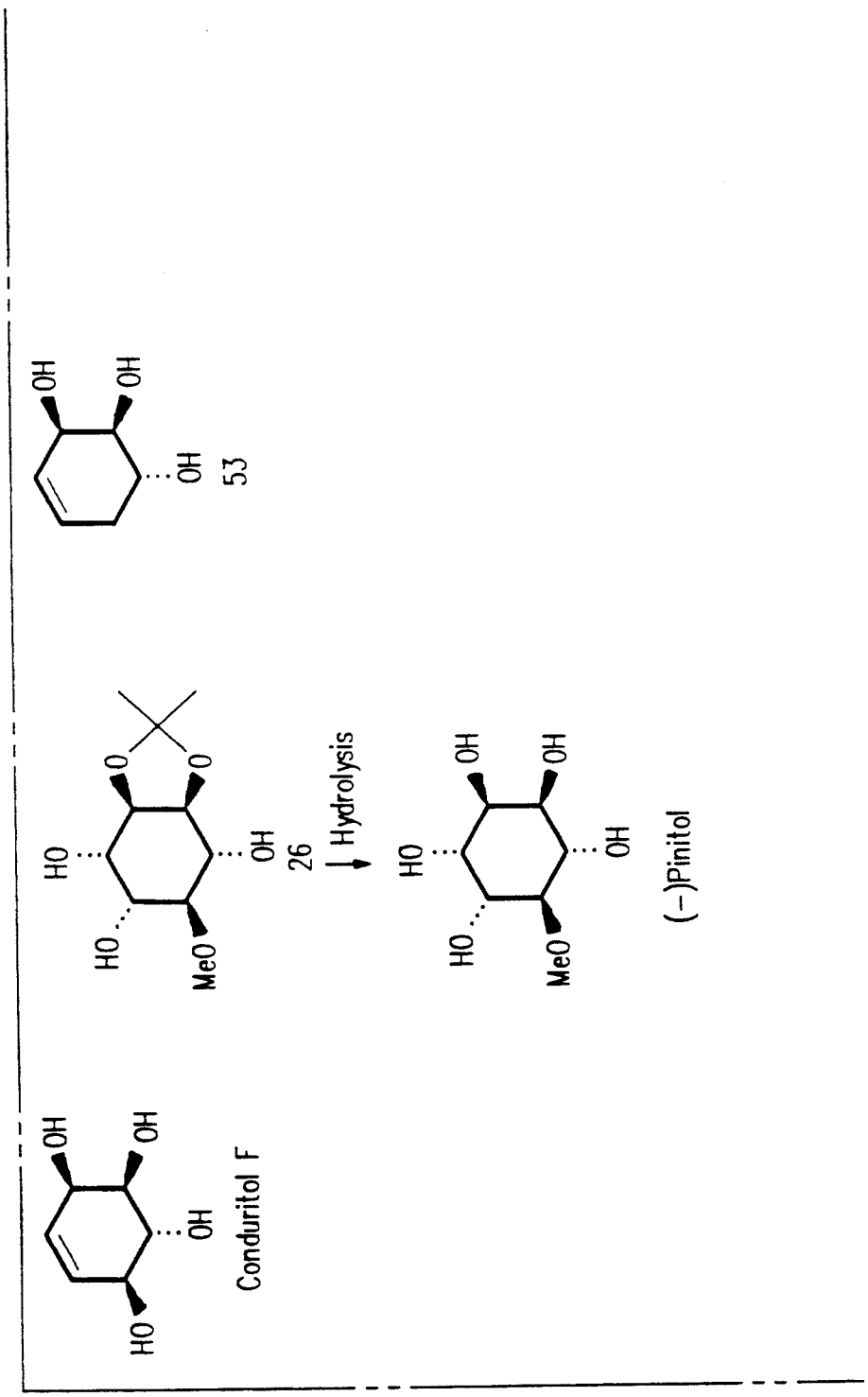

A generalized scheme for synthesis of cyclitols from arene diols is shown in FIG. 1. Although chloro and bromo diols are shown in FIG. 1, the same general scheme can be used with other substituted arene diols of formula (I) above.

Cyclitols having three hydroxy groups 51a and 51b can be produced by reduction of epoxides (2a or 2b respectively). Epoxides 2a and 2b are formed from the acetonide (AA). Depending on whether syn or anti addition of the subsequent functional group is desired, the free diol may be used instead of the acetonide. Compound 51a or 51b (a=Cl, b=Br) is then reduced to 52 and finally deprotected to compound 53, or 3,4,5-trihydroxycyclohex-1-ene. This example illustrates the functional stereocontrol inherent in all subsequent examples disclosed herein and also illustrates how any derivatives of cyclitols, regardless of stereochemical disposition of hydroxyl groups may be obtained. Each synthetic operation controls the regio- and stereochemistry of the next chiral center.

Use of an alcohol (ROH) or water yields -OR or -OH at C4. Anti addition of the fourth functional group can also be achieved directly from the acetonide (AA) by sequential treatment with singlet oxygen and thiourea such as in the attainment of 8.

Additional functional groups can be added by hydroxylations, epoxidations, ozonolysis, nucleophilic additions, and other processes that proceed with defined stereochemistry. Addition of the epoxide functionality is anti if the group on the preceding carbon is protected (i.e., -OR) or syn if the preceding carbon group is unprotected (i.e., -OH). For example, if C4 bears -OCH$_3$, addition of the epoxide function is anti. Treatment of the epoxide with acidic water or alcohol (ROH) as shown in FIG. 1 provides -OH or -OR functionality at the epoxide carbons (ex: 23 and 24a or 24b). After further reduction, the resulting protected tetrol 24a, 24b can be further functionalized by treatment with either osmium tetroxide (syn addition, 26) or MCPBA and acidic alcohol (ROH) (anti addition, 23).

Within the context of this general scheme relative stereochemistry can be controlled at a given step by controlling the character of the functional group on the preceding carbon. For example, if a given step will add functionality at C4 and C5, relative stereochemistry can be controlled by the character of the functionality on C3. If the preceding functionality is -OH, the next functionality will be added syn; if the preceding functionality is protected (i.e., -OR), the next functionality will be added anti. Similarly, use of acidic ROH instead of acidic water to add functionality avoids making symmetrical intermediates which lead to meso compounds and loss of control of stereospecificity in the reaction.

Since only the syn or anti distinction is used throughout the general scheme, each center can be formed either "up" or "down" at will by using the variables disclosed herein. If the original diol needs to be trans in order to achieve the desired configuration at C2 and C3, either carbon center can be inverted using the Mitsunobu process described in Hudlicky et al., J. Org. Chem. 54:4239, 1989.

Thus any cycitol from trihydroxycyclohexane to hexahydroxylated compounds such as pinitol can be obtained. By judicious use of symmetry considerations, both enantiomers may be attained from the same enantiomer of chloro- or bromo diol as illustrated on the pinitol synthesis.

It will be apparent to those skilled in the art that isotopically labelled cyclitols can also be prepared in accordance with the present invention by using isotopically labelled reagents at appropriate stages in the synthetic process.

All hydrolytic reactions were carried out in a nitrogen or argon atmosphere, with standard techniques for the exclusion of air and moisture. Glassware used for moisture-sensitive reactions was flame-dried with an internal inert gas sweep. THF, ethyl ether, DME and benzene were distilled from benzophenone ketyl; dichloromethane and toluene from calcium hydride.

Preparation of compounds A, C, AA, D, 3b, 21, 8, 2a and 2b as shown in FIG. 1, is provided in commonly assigned U.S. patent application Ser. No. 07/802,943 (a continuation-in-part of U.S. Ser. No. 07/480,491 filed Feb. 16, 1990, which disclosure is incorporated herein by reference.

All references cited herein are incorporated by reference as if fully set forth.

EXPERIMENTAL (1S,2R,3R,4R)-1,2-Dihydroxy-3,4-di-O-isopropylidene cyclohex-5-ene 31)

Bu$_3$SnH (384 mg, 1.32 mmol) was added to a mixture of AIBN (217 mg, 0.66 mmol) and the vinyl bromide 15 (175 mg, 0.66 mmoL) in dry toluene (20 mL). The reaction mixture was refluxed for 3 h. The solvent was evaporated and the residue was purified by flash column chromatography on silica gel (7.5:2.5 EtOAc/Hexane) to afford 96.9 mg (0.52 mmoL, 79%) of the pure product as a white solid. An analytical sample was obtained by sublimation. mp=119.0° C. $R_f$=0.27 (EtOAc/Hexane, 4:1). $[\alpha]^{20}_D$ = −70.8° (c 0.25, CHCl$_3$). IR (KBr) $\nu$ 3419, 3044, 2988, 1372, 1053 cm$^{-1}$. $^1$H-NMR (CDCl$_3$) $\delta$ 5.83 (2H, m), 4.62 (1H, dd, J=6.5, 2.3), 4.07 (2H, dd, J=8.7, 6.7), 3.55 (1H, t, J=9.0), 3.23 (2H, bs), 1.49 (3H, s), 1.37 (3H, s). $^{13}$C-NMR (CDCl$_3$) $\delta$ 133.5 (CH), 123.5 (CH), 110.5 (C), 77.6 (CH), 75.0 (CH), 72.6 (CH), 70.4 (CH), 28.1 (CH$_3$), 25.7 (CH$_3$). MS (Cl) m/z (relative intensity) 187 (M.$^+$, 12), 171 (28), 129 (29), 111 (100), 83 (36). Anal Calcd for C$_9$H$_{14}$O$_4$: C, 58.05; H, 7.58. Found: C, 58.04; H, 7.63.

Conduritol F

Acetonide 31 made as described above, (209 mg, 1.12 mmol) was dissolved in a mixture of AcOH/THF/H$_2$O (2:1:1, 3 mL). The solution was stirred at 60° C. for 6 h. The solvent was evaporated and 164 mg (1.1 mmol, 99% yield) of Conduritol F was obtained. An analytical sample was obtained after recrystallization from MeOH-ether. $R_f$=0.18 (CHCl$_3$—MeOH, 4:1); mp=131°-132° C. (lit* 129°-130° C.); $[\alpha]^{20}_D$= −84 (c 0.71, MeOH) (lit.* −70.5°, MeOH); IR (KBr) $\nu$ 3283, 2920, 1420, 1102, 1061 cm$^{-1}$; $^1$H NMR (CDCl$_3$) $\delta$ 5.79

(1H, ddd, J=10.0, 4.7, 1.9 Hz), 5.71 (1H, dd, J=10.0, 1.9 Hz), 4.15 (1H, t, J=4.3 Hz), 3.92 (1H, dt, J=7.5, 1.6 Hz), 3.61 (1H, dd, J=10.4, 7.7 Hz), 3.41 (1H, dd, J=10.4, 4.2 Hz); $^{13}$C NMR (CDCl$_3$) δ 133.8 (CH), 128.1 (CH), 74.1 (CH), 73.8 (CH), 72.7 (CH), 68.0 (CH); MS (EI) m/z (rel. intensity) 128 (8), 110 (11), 99 (98), 86 (100); Anal. Calcd for C$_6$H$_{10}$O$_4$: C, 49.31; H, 6.90; Found: C, 49.30; H, 6.94.

*(a) M. Nakajima, I. Tomida and S. Takei, *Chem. Ber.* 1959, 92, 163; (b) H. Paulsen, W. Roben and F. R. Heiker, *Chem. Ber.* 1981, 114, 3242; (c) H. Secen, Y. Sutbeyaz and M. Balci, *Tetrahedron Letters* 1990, 31, 1323; (d) C. L. Drian, J-P. Vionnet and P. Vogel, *Hel. Chim. Acta* 1990, 73, 161; (e) S.V. Ley and A. J. Redgrave, *Synlett* 1990, 393.

(1R,2R,3S,4R)-1,2-Dihydroxy-3,4-di-O-isopropylidene cyclohex-5-ene 14

Method A

To a solution of 3b (20 mg, 0.075 mmol) in dry THF (5 mL) a suspension of LiAlH$_4$ (66 mg in 14 mL of THF) was added. The reaction mixture was stirred at room temperature (rt) for 8 h. The reaction was quenched with brine (5 mL) and extracted with EtOAc (5×5 mL); the organic extracts were dried (Na$_2$SO$_4$) and evaporated. Purification by flash chromatography produced 12.5 mg of 14 (0.067 mmol, 90%). R$_f$=0.27 (EtOAc/hexane, 2:1).

Method B

To a solution of 3b (662.5 mg, 2.5 mmol) and AIBN (864 mg, 6 mmol) in Toluene (30 mL) tributyltin hydride (1.61 mL, 6 mmol) was added; the mixture was refluxed under Argon atmosphere for 5 h. The solvent was removed under vacuum, the residue was taken in EtOAc (20 mL) and washed with brine (5×5 mL); the organic solution was dried and evaporated. Flash chromatography (silica gel; EtOAc/hexane, 2:1) afforded 420 mg of 14 (2.25 mmol, 90%). mp=66°-67° C.; R$_f$=0.27 (EtOAc/hexane, 2:1); [α]$^{25}$$_D$=−151.3° (c, 2.82; CHCl$_3$); IR (KBr) 3350, 3000, 2940, 1650 cm$^{-1}$; $^1$H NMR (CDCl$_3$) δ 5.90 (d, J=1.8 Hz, 1H), 4.64 (dd, J=5.9, 1.8 Hz, 1H), 4.34 (t, J=6.3 Hz, 1H), 4.28 (m, 1H), 3.95 (dd, J=6.3, 3.8 Hz, 1H), 1.42 (s, 3H), 1.36 (s, 2H); $^{13}$C NMR (CDCl$_3$) δ 130.0, 127.4, 109.4, 75.9, 71.9, 71.2, 66.0, 27.9, 25.9; mass spectrum (EI, 70 eV) m/e (rel. intensity) 171 (M-15, 0.95); Anal. calcd for C$_9$H$_{14}$O$_4$: C, 58.06; H, 7.53; Found: C, 57.97; H, 7.57.

(1S,2R,3R,4S,5R,6S)-2,3-Dihydroxy-4,5-di-O-isopropylidene-7-oxa-bicyclo[4.1.0]heptane 22

To a solution of cyclohexene 14 (372 mg, 2.00 mmol) in CH$_2$Cl$_2$ (20 mL) was added mCPBA (610 mg, 3.54 mmol). The mixture was stirred for 24 h at room temperature. The reaction mixture was washed with concentrated aqueous sodium bisulfite and sodium bicarbonate, dried (Na$_2$SO$_4$), and concentrated leaving a solid. Purification by flash chromatography (10% deactivated silica gel, EtOAc/hexane, 9:1) afforded 355 mg (1.76 mmol, 88%) of colorless crystals: mp=72°-72.5° C. (recrystallized from EtOAc/hexane, 9:1); R$_f$=0.55 (EtOAc/hexane, 9:1); [α]$^{25}$$_D$=−2.2° (c 4.02, CHCl$_3$); FTIR (KBr) 3500-3250, 3010, 2960, 2930, 1665 cm$^{-1}$; $^1$H NMR (CDCl$_3$) δ 4.57 (d, J=5.8 Hz, 1H), 4.53 (m, 1H), 4.24 (br s, 1H), 4.05 (m, 1H), 3.54 (m, 1H), 3.40 (m, 1H), 3.13 (d, J=7.4 Hz, 1H), 2.90 (d, J=11.6 Hz, 1H), 1.43 (s, 3H), 1.36 (s, 3H); $^{13}$C NMR (CDCl$_3$) δ 110.0 (C); 77.0 (CH); 69.9 (CH), 68.6 (CH), 64.4 (CH), 57.8 (CH), 56.0 (CH), 27.4 (CH$_3$), 25.0 (CH$_3$); mass spectrum (EI, 70 eV) m/e (rel intensity) 187 (M-CH$_3$, 0.66), 109 (0.57), 81 (0.50), 73 (0.66), 69 (0.45), 59 (1.00); Anal. calcd for: C$_9$H$_{14}$O$_5$: C, 53.47; H, 6.93. Found: C, 52.42; H, 7.08.

(1R,2R,3R,4S,5R,6S)-2,3,6-Trihydroxy-4,5-di-O-isopropylidene-1-O-methylcyclohexane 23

To a solution of epoxide 22 made by the process described above, (101 mg, 0.50 mmol) in methanol (50 mL) was added 5 g of neutral alumina (dried at 110° C. for 4 h). The reaction mixture was refluxed for 24 h with vigorous stirring. The mixture was filtered and the alumina was washed with hot methanol (2×15 mL). The combined organic fractions were evaporated and the residue was purified by flash chromatography (silica gel, EtOAc) affording 63 mg (0.30 mmol, 60%) of colorless crystals: mp=78.5°-79° C.; R$_f$=0.27 (EtOAc); [α]$^{25}$$_D$=+59.3° (c 0.88, CH$_3$OH); FTIR (KBr) 3600-3200, 2980, 2930, 1450, 1380 cm$^{-1}$; $^1$H NMR (CDCl$_3$) δ 4.31 (dd, J=6.0, 4.3 Hz, 1H), 4.19 (m, 2H), 3.84 (m, 1H), 3.74 (m, 1H), 3.62 (s, 3H), 3.34 (dd J=7.5, 7.5 Hz, 1H), 2.88 (m, 1H), 2.81 (d, J=3.4 Hz, 1H), 2.18 (s, 1H), 1.49 (s, 3H), 1.37 (s, 3H); $^{13}$C NMR (CDCl$_3$) δ 109.6 (C), 82.3 (CH), 78.7 (CH, 76.6 (CH), 74.5 (CH), 71.7 (CH), 69.9 (CH), 59.9 (CH$_3$), 27.8 (CH$_3$), 25.5 (CH$_3$); mass spectrum (CI, 70 eV) m/e (rel intensity) 235 (M+1, 1.00), 219 (0.53), 177 (0.42), 159 (0.20), 141 (0.37), 127 (0.32); Anal. calcd for C$_{10}$H$_{18}$O$_6$: C, 51.28; H, 7.74. Found: C, 50.42; H, 7.76.

(+)-Pinitol

To a solution of triol 23 made by the process described above, (13.5 mg. 0.064 mmol) in 3 mL of acetone-H$_2$O (2:1) were added 3 drops of concentrated HCl. The mixture was stirred at rt for 30 min, then concentrated under vacuum to afford (+)-pinitol quantitatively as colorless crystals: mp=184.5°-185° C.; [α]$^{25}$$_D$=+64.6° (c 1.0, H$_2$O); $^1$H NMR data matched those reported. [Ley, S. V.; Sternfeld, F. *Tetrahedron* 1989, 45, 3463].

(3R,4R,5S,6S)-1-Chloro-4-hydroxy-5,6-di-O-isopropylidene-3-O-methylcyclohex-1-ene 24a To a solution of epoxide 2a (1.03 g. 5.0 mmol) in MeOH (16 mL) and CHCl$_3$ (8 mL) was added camphorsulfonic acid (CSA) (183 mg). The mixture was stirred at room temperature for 45 min. The solution was poured into CH$_2$Cl$_2$ (50 mL), washed with satd. aq. NaHCO$_3$ (2×50 mL), and H$_2$O (50 mL), then dried (MgSO$_4$), filtered, and concentrated leaving a yellow oil which after purification by flash chromatography (silica gel, hexane-EtOAc, 1:1) afforded 800 mg (4.3 mmol, 86%) of methyl ether 24a as an oil: R$_f$=0.25 (hexane/EtOAc, 1:1); [α]$^{25}$$_D$=+10.7° (c 1.0, CHCl$_3$); FTIR (neat) 3452, 2987, 2934, 1650, 1381 cm$^{-1}$; $^1$H NMR (CDCl$_3$) δ 6.02 (d, J=1.4 Hz, 1H), 4.58 (d, J=6.4 Hz, 1H), 4.14 (dd, J=8.4, 6.4 Hz, 1H), 3.6-3.7 (m, 2H), 3.44 (s, 3H), 2.9 (br s, 1H), 1.52 (s, 3H), 1.39 (s, 3H); $^{13}$C NMR (CDCl$_3$) δ 129.1, 127.9, 111.3, 79.4, 77.5, 75.8, 72.6, 57.3, 28.0, 25.3; mass spectrum (Cl, 70 eV) m/e (rel. intensity) 235 (M+1, 0.55), 219 (0.17), 203 (0.21), 159 (0.21), 145 (1.00); HRMS calcd for C$_{10}$H$_{15}$ClO$_4$: 234.0737;

(3R,4R,5S,6S)-1-Bromo-4-hydroxy-5,6-di-O-isopropylidene-3-O-methylcyclohex-1-ene 24b To a solution of epoxide 2b (750 mg, 3.036 mmol) in MeOH—CHCl$_3$ (2:1, 25 mL). was added CSA (133 mg, 0.572 mmol). The reaction mixture was stirred at rt for 45 min; then the reaction mixture was concentrated and extracted with ethyl acetate (2×20 mL). The organic layer was washed with satd aq NaHCO$_3$ (10 mL), dried (Na$_2$SO$_4$) and the solvent evaporated. After purification by flash chromatography (silica gel; hexanes/ethyl acetate, 1:1) 750 mg (2.702 mmol, 89%) of a colorless liq. was obtained. R$_f$=0.4 (hexanes/ethyl acetate, 1:1); [α]$^{25}_D$= +27.2° (c 0.235; MeOH); FTIR (neat) 3442, 2987, 2935, 2830, 1645 cm$^{-1}$; $^1$H-NMR (acetone-d$_6$) δ 6.28 (s, 1H), 4.68 (d, J=6.3 Hz, 1H), 4.17 (m, 1H), 3.66 (m, 2H), 3.48 (s, 3H), 1.55 (s, 3H), 1.42 (s, 3H); $^{13}$C-NMR (acetone-d$_6$) δ 133.6, 119.6, 110.2, 81.0, 78.7, 77.4, 72.3, 57.4, 27.9, 25.7; mass spectrum (EI, 70 eV) m/e (rel intensity) 280 (M$^+$, 0.64), 278 (0.64), 265 (0.80), 263 (0.80), 205 (0.24), 203 (0.24), 191 (0.36), 124 (0.48), 101 (1.00); Anal. calcd for C$_{10}$H$_{15}$BrO: C, 43.03; H, 5.41. Found: C, 42.92; H, 5.43.

(3R,4R,5S,6S)-3-O-Methyl-4-hydroxy-5,6-di-O-isopropylidene cyclohex-1-ene 25

Method A

To a solution of bromoolefin 24b made by the process described above, (60 mg, 0.216 mmol) in anhydrous THF (3 mL), was added LiAlH$_4$ (8.4 mg, 0.22 mmol) under Argon atmosphere. The reaction mixture was stirred at rt for 8 h. The reaction was quenched with brine and extracted with ethyl acetate (2×20 mL). The organic layers were dried (Na$_2$SO$_4$), and concentrated leaving yellow oil. Purification by flash chromatography (silica gel; hexanes/ethyl acetate, 1:2) afforded 36.3 mg (0.18 mmol, 85%) of cyclohexene 25 as an oil: R$_f$=0.34 (hexanes/ethyl acetate, 1:2); [α]$^{25}_D$= −36.7° (c 0.36, MeOH); FTIR (neat) 3461, 1695, 1381 cm$^{-1}$; $^1$H NMR (CDCl$_3$) δ 5.94 (d, J=10.5 Hz, 1H), 5.88 (ddd, J=10.5, 2.9, 1.6 Hz, 1H), 4.63 (dd, J=7.0, 2.9 Hz, 1H); 4.12 (dd, J=8.3, 7.0 Hz, 1H), 3.65 (m, 2H), 3.48 (s, 3H), 2.2 (br s, 1H), 1.51 (s, 3H), 1.39 (s, 3H); $^{13}$C NMR (CDCl$_3$) δ 131.0, 124.1, 110.5, 79.8, 73.3, 72.4, 57.2, 28.1, 25.7; mass spectrum (Cl, 70 eV) m/e (rel intensity) 201 (M+1, 0.07), 199 (0.27), 185 (1.00), 125 (0.71), 111 (1.00); HRMS calcd for C$_9$H$_{13}$O$_4$: (M—CH$_3$) 185.0814; Found: 185.0854.

Method B

The above procedure was repeated using vinylchloride 24a made by the process described above, with heating to reflux, to afford cyclohexene 25 in 54% yield, identical in all respects to the material obtained above.

(1S,2S,3S,4R,5S,6R)-2,3,6-Trihydroxy-4,5-di-O-isopropylidene-1-O-methylcyclohexane 26

To a solution of olefin 25 (150 mg, 0.75 mmol) in acetone-H$_2$O (3:1, 6.8 mL), NMO (67 mg) and 0.2 mL of a 2.5 wt % solution of OsO$_4$ in t-BuOH were added, at rt. The reaction mixture was stirred at rt for 2 days, when and additional 0.2 ml of OsO$_4$ solution was added. The reaction was continued for 3 more days (analysis by TLC showed some starting material left). The reaction mixture was quenched with 10 mL of 15% NaHSO$_3$ and saturated with NaCl, and was extracted with ethyl acetate (2×15 mL). The combined organic layers were dried over Na$_2$SO$_4$, and concentrated to afford 171 mg of an oil which crystallized upon refrigeration. Purification by flash chromatography (silica gel; hexanes/ethyl acetate, 1:5) produced 110 mg (0.47 mmol, 62.7%) of triol 26 and 58 mg of recovered starting material. Triol 26: mp=81.5° C.; R$_f$=0.14 (ethyl acetate/hexanes, 4:1); [α]$^{25}_D$= −58.0° (c 0.25, MeOH); FTIR (KBr) 3395, 2989, 2939, 1382, 1065 cm$^{-1}$; $^1$H NMR (acetone-d$_6$) δ 4.40 (br s, 1H), 4.33 (br d, J=4.3 Hz, 1H), 4.21 (dd, J=6.2, 4.3 Hz, 1H), 4.07 (dd, J=7.6, 6.2 Hz, 1H), 3.98 (m, 1H), 3.72 (m, 1H), 3.53 (m, 1H), 3.47 (s, 3H), 3.21 (dd, J=8.4, 6.8 Hz, 1H), 3.10 (br s, 1H), 1.37 (s, 3H), 1.26 (s, 3H); $^{13}$C NMR (acetone-d$_6$) δ 109.3, 84.5, 79.9, 78.2, 75.6, 72.8, 71.1, 59.6, 28.2, 25.8; Anal. calcd for C$_{10}$H$_{18}$O$_6$: C, 51.28; H, 7.74. Found: C, 51.22; H, 7.80.

(−)-Pinitol

To a solution of triol 26 made by the process as described above, (10 mg, 0.043 mmol) in acetone-H$_2$O (2:1, 3 mL) was added 3 drops of concentrated HCl. The reaction mixture was stirred at rt for 10 min. Solvent was removed under vacuum leaving 8.0 mg (0.041 mmol, 96%) of a colorless solid: mp=184.5°–185.0° C.; [α]$^{25}_D$= −61.5° (c, 0.19, H$_2$O); $^1$H NMR data matched those reported. [Ley, S. V.; Sternfeld, F. *Tetrahedron* 1989, 45, 3463].

(4R,5S,6R)-4-O-(t-Butyldimethylsilyl)-5,6-di-O-isopropylidenelcyclohex-2-en-1-one 28

To a solution of t-butyldimethylchlorosilane (1.00 g, 6.67 mmol) in dry DMF (4 mL), diisopropylethylamine (1.5 mL, 8.58 mmol) was added at rt. After the hydrochloric acid was removed by the stream of Argon, the enone 8 (415.4 mg, 2.258 mmol) in dry DMF (4 mL) was added dropwise. The reaction mixture was stirred at rt for 8.5 h; then brine (10 mL) and EtOAc (20 mL) were added, the stirring was continued for 10 min. The layers were separated and the aqueous layer was washed with ethyl acetate (2×4 ml). The combined organic fractions were washed with brine (3×5 mL), dried (Na$_2$SO$_4$), and the solvent was removed under reduced pressure affording a dark oil which was immediately purified by flash chromatography (silica gel, ethyl acetate/hexane, 3:7) producing 579.5 mg (5.74 mmol, 86%) of a viscous oil which solidified upon refrigeration (mp=50°–54° C.). This product was suitable for the next reaction. An analytical sample was obtained by distillation of the solid (Kugelrohr, 100°–110° C./0.1 torr). mp=56.5°–57° C.; R$_f$=0.35 (hexanes/ethyl acetate, 9:1); FTIR (neat) 2955, 2931, 2858, 1694, 1383, 1375 cm$^{-1}$; $^1$H NMR (CDCl$_3$) δ 6.88 (ddd, J=10.2, 3.8, 1.0 Hz; 1H), 6.09 (dd, J=10.2, 1.0 Hz; 1H); 4.56 (m, 1H), 4.44 (m, 2H), 1.41 (s, 3H), 1.40 (s, 3H), 0.92 (s, 9H), 0.17 (s, 3H), 0.15 (s, 3H); $^{13}$C NMR (CDCl$_3$) δ 194.3, 148.4, 127.9, 110.1, 79.7, 74.4, 67.2, 27.4, 25.7, 18.0, −4.7; mass spectrum (EI, 70 eV) m/e (rel intensity) 298 (M$^+$, 0.03), 283 (0.05), 241 (0.12), 198 (0.35), 183 (1.00); Anal. calcd for C$_{15}$H$_{26}$SiO$_4$: C, 60.36; H, 8.78. Found: C, 60.23; H, 8.81.

(2S,3S,4R)-4-O-(t-Butyldimethylsilyl)-2,3-di-O-isopropylidenecyclohexan-1-one 27

To a solution of enone 28 (116 mg, 0.374 mmol) in MeOH (6 mL) was added 10% Pd/C (9.5 mg). The mixture was hydrogenated (50 psi) in a Parr vessel at room temperature for 5.5 h. The reaction mixture was filtered through Celite ®; evaporation of the solvent produced 109 mg (0.362 mmol, 97%) of a colorless liquid, which crystallized upon refrigeration. This product was used without further purification. An analytical sample was obtained by distillation (Kugelrohr; 100°/0.2 torr). mp=44.5°–45° C.; R$_f$=0.58 (hexanes/ethyl acetate; 8:2); [α]$^{25}_D$= +2.14 (c 0.42, MeOH); FTIR (neat) 2954, 2931, 2857, 1731, 1256 cm$^{-1}$; $^1$H NMR (CHCl$_3$) δ 4.3 (m, 2H), 4.15 (m, 1H), 2.7 (ddd, J=15.2, 12.7, 6.2 Hz, 1H), 2.32 (ddd, J=15.2, 4.8, 3.0 Hz, 1H), 2.12 (td, J=13.9, 4.8 Hz, 1H), 1.9 (dddd, J=13.9, 6.2, 3.0, 0.9 Hz, 1H), 1.4 (s, 3H), 1.34 (s, 3H), 0.87 (s, 9H), 0.09 (s, 3H), 0.08 (s, 3H); $^{13}$C NMR (CDCl$_3$) δ 207.8 (C), 110.4 (C), 80.9 (CH), 78.1 (CH), 67.1 (CH), 33.3 (CH), 27.4 (CH$_2$), 27.0 (CH$_3$), 25.6 (CH$_3$), 17.9 (CH), −4.9 (CH$_3$); Anal. Calcd. for C$_{15}$H$_{28}$O$_4$Si: C, 59.96; H, 9.39. Found: C, 59.86; H, 9.43.

(1R,2R,3R,4R)-1-Hydroxy-2,3-di-O-isopropylidene-4-O-(t-butyldimethylsilyl)cyclohexane 33

To a solution of ketone 27 made by a process as described above, (255 mg. 0.89 mmol) in THF (4 mL) was added a 1.0M solution of L-selectride (1.8 mL, 1.8 mmol) in THF at 0° C. The reaction was allowed to warm to room temperature and stirred for 3 h. The reaction was quenched by the addition of H$_2$O (1 mL), EtOH (3 mL), 3N aq NaOH (4 mL), and 30% aq H$_2$O$_2$ (3 mL). The aqueous phase was saturated with K$_2$CO$_3$ and extracted with EtOAc (5×20 mL). The organic phase was dried (MgSO$_4$), filtered, and concentrated leaving a yellow oil which after purification by flash chromatography (silica gel, hexane-EtOAc, 1:1) afforded 193 mg (68 mmol, 76%) of pure alcohol 33: R$_f$=0.45 (hexane/EtOAc, 1:1); [α]$^{25}_D$= −40.2° (c 0.39, CHCl$_3$); FTIR (neat) 3440, 2987, 2930, 1380, 1370 cm$^{-1}$; $^1$H NMR (CDCl$_3$) δ 4.28 (dd, J=6.0, 3.8 Hz, 1H), 3.91 (t, J=5.7 Hz, 2H), 3.76–3.68 (m, 1H), 2.20 (br s, 1H) 1.82–1.70 (m, 2H), 1.65–1.50 (m, 1H), 1.46 (s, 3H), 1.32 (s, 3H), 1.35–1.25 (m, 1H), 0.83 (s, 9H), 0.03 (s, 3H), 0.01 (s, 3H); $^{13}$C NMR (CDCl$_3$) δ 108.9, 80.4, 71.1, 67.5, 27.4, 27.1, 25.7, 25.4, 17.9, −4.73, −4.88; mass spectrum (El, 70 eV) m/e (rel intensity) 287 (M-15, 0.33), 187 (0.30), 169 (0.92), 143 (0.21), 75 (1.00); Anal. calcd for C$_{15}$H$_{30}$O$_4$Si: C, 59.56; H, 10.00. Found: C, 59.47; H, 10.05.

(−)-Dihydroconduritol C

To a solution of alcohol 33 made by a process as described above, (35 mg, 0.12 mmol) in aceton-H$_2$O (1:1, 2 mL) was added dropwise concentrated HCl until pH=2. The solution was stirred at rt for 8 h. Solvent and HCl were removed under vacuum leaving 16 mg (0.11 mmol, 92%) of pure tetrol whose spectral data were in agreement with literature values:** mp=157°-158° C.; [α]$^{25}_D$= −36° (c 0.10, D$_2$O); $^1$H NMR (D$_2$O) δ 4.83 (s, 4H), 4.00 (t, J=2.7 Hz, 1H), 3.77–3.61 (m, 2H), 3.41–3.32 (m, 1H), 1.89 (ddd, J=12.5, 8.1, 4.0 Hz, 1H) 1.71–1.53 (m, 1H), 1.25 (ddd, J=17.5, 11.8, 5.5 Hz, 1H); $^{13}$C NMR (D$_2$O) δ 73.9, 72.6, 69.2, 68.6, 27.3, 24.7.

**(a) Le Drian C.; Vieira, E.; Vogel, P. Helv. Chim. Acta 1989, 72, 338. (b) Le Drian, C.; Viommet, J.-P.; Vogel, P. Helv. Chim. Acta 1990, 73, 161. (c) Gorin, 2P. A. J.; Mazurek, M. Carbohydrate Res. 1973, 27, 325. (d) Barbezat, P.; Reymond, D.; Posternak, T. Helv. Chim. Acta 1967, 50, 1811.

(1R, 2R, 3R,4R)-1-Hydroxy-2,3-di-O-isopropylidene-4-O-(t-butyldimethylsilyl)cyclohex-5-ene 29

To a solution of enone 28 made by a process as described above, (107 mg, 0.359 mmol) in THF (0.15 mL) at 0° C. was added 0.35 mL of 1.0M L-selectride (0.350 mmol). The solution was stirred for 50 min. The reaction was quenched by the addition of 10% NaOH (1 mL) followed by 30% H$_2$O$_2$ (1 mL); stirring was continued at 0° C. for an additional 20 min. The aqueous layer was saturated with K$_2$CO$_3$ and extracted with EtOAc (4×3 mL). The combined organic fractions were dried (Na$_2$SO$_4$), filtered, and concentrated leaving a yellow oil, which after purification by flash chromatography (silica gel, hexane-EtOAc, 8:2) afforded 55 mg (0.183 mmol, 51%) of alcohol 29: R$_f$=0.44 (hexane/EtOAc, 7:3); [α]$^{25}_D$= −120.4° (c 0.22, MeOH); FTIR (neat) 3476, 2955, 2930, 2857, 1472 cm$^{-1}$; $^1$H NMR (CDCl$_3$) δ 5.91 (s, 1H), 5.90 (s, 1H), 4.48 (dd, J=6.8, 4.4 Hz, 1H), 4.37 (dd, J=7.7, 4.4 Hz, 1H), 4.32–4.24 (m, 2H), 2.55 (d, J=7.7 Hz, 1H), 1.38 (s, 3H), 1.35 (s, 3H), 0.84 (s, 9H), 0.06 (s, 3H), 0.03 (s, 3H); $^{13}$C NMR (CDCl$_3$) δ 132.9, 132.1, 109.1, 79.0, 75.8, 67.3, 65.0, 26.3, 25.7, 24.6, 18.0, −4.2, −4.5; mass spectrum (70 eV) m/e (rel intensity) 184 (M+, 0.11), 169 (0.26), 155 (0.20), 100 (0.66), 97 (1.00); Anal. calcd for C$_{15}$H$_{28}$O$_4$Si: C, 59.96; H, 9.39. Found: C, 59.85; H, 9.40.

Conduritol C

A solution of olefin 29 made by a process as described above, (150 mg, 0.5 mmol) in acetic acid-water-THF (2:1:1, 4 mL) was stirred at 50°-55° C. for 6 h. The reaction mixture was diluted with EtOAc and concentrated under reduced pressure. This procedure was repeated twice. The crude product was recrystallized from MeOH-ether to afford 72.1 mg (0.4938 mmol, 98%) of Conduritol C. mp=128°-131° C.; [α]$^{23}_D$= −193° (c 0.3; H$_2$O). A $^1$H NMR obtained matched with the spectrum kindly furnished to us by Prof. P. Vogel (Lausanne).

Conduritol A

Reduction of 28 made by a process as described above, with NaBH$_4$ afforded a mixture of 29 and 30. Deprotection of 30 with AcOH and H$_2$O gave conduritol A (meso).

(1S, 2R, 3S, 4R)-2,3-O-isopropylidene-1,4-dihydroxycyclohex-5-ene, Conduritol A acetonide 30

Endoperoxide 21 was dissolved in Et$_2$O (50 mL) and two drops of water was added. The solution was treated with aluminum amalgam (prepared from 0.5 g of aluminum foil). The reaction mixture was stirred for 25 min, whereupon filtration over Celite ® and evaporation of the solvent gave 310 mg (1.67 mmol, 77%) of essentially pure acetonide of Conduritol A 30, which was recrystallized from CH$_2$Cl$_2$-hexane. mp=100.5°-101° C. (lit$^a$ 101°-102° C.); $^1$H NMR δ (CDCl$_3$) 5.88 (2H, s), 4.20 (4H, s), 2.49 (2H br s), 1.43 (3H, s), 1.34 (3H, s). [(a) S. Knapp, R. M. Ornaf and K. E. Rodrigues, J. Chem. Soc. 1983, 105, 5495; Y. Sütbeyaz, H. Secen and M. Balci J. Chem. Soc. Chem. Commun. 1988, 1330.]

(−)Conduritol E

Acetonide 14 (89 mg, 0.478 mmol) was dissolved in a mixture of AcOH/THF/H$_2$O (2:1:1, 3 mL). The solution was stirred at 60° C. for 4 h. The solvent was evaporated and 69 mg (0.475 mmol, 99% yield) of Conduritol E was obtained. An analytical sample was obtained by recrystallization from MeOH-ether. R$_f$=0.18 (CHCl$_3$—MeOH, 4:1); mp=192°-193° C. (lit.* 193° C.); [α]$^{20}_D$= −330° (c 4.5, H$_2$O) (lit*+332); IR (KBr) υ 3382, 2917, 1475, 1097, 1030 cm$^{-1}$; $^1$H NMR (D$_2$O) δ 5.72 (2H, m), 4.15 (2H, m), 3.76 (2H, m); $^{13}$C NMR (D$_2$O) (Ref. acetone) δ 127.3 (2 CH), 66.7 (2 CH), 64.2 (2 CH); MS (Cl) m/z (rel. intensity) 147 (M+, 6), 129 (37), 111 (98), 83 (100); Anal. Calcd for C$_6$H$_{10}$O$_4$: C, 49.31; H, 6.90; Found: C, 49.21; H, 6.90.

*Dictionary of Organic Compounds Vol. 2. p. 1374, 5th ed. 1982.

(1S, 2S, 3R)-6-Chloro-3-hydroxy-1,2-O-isopropylidene cyclohex-5-ene 51a

Epoxide 2a (300 mg, 1.4815 mmol) was dissolved in Et$_2$O (3 mL) and added to a solution of LiAlH$_4$ (56.2 mg, 1.4815 mmol) in Et$_2$O (10 mL) and the mixture was refluxed for 5 h. Ethyl acetate (5 mL) was added, followed by 10% NaOH solution (10 mL). Organic layer was washed with H$_2$O (5 mL), brine (5 mL), and dried with Na$_2$SO$_4$. Solvent was evaporated and alcohol was purified by flash chromatography (silica gel; hexane-etyhl acetate, 6:4) to yield 241 mg (1.18 mmol, 80% yield) of pure chloroalcohol 51a. R$_1$=0.34 (hexane-ethyl acetate, 3:2); $[\alpha]^{20}_D$=52.5° (c 1.9, CHCl$_3$), IR (KBr) $\upsilon$ 3424, 2988, 1654, 1382, 1219, 1074 cm$^{-1}$; $^1$H NMR (CDCl$_3$) $\delta$ 5.94 (1H, dd, J=5.4, 3.4 Hz), 4.56 (1H, d, J=6.0 Hz), 4.08 (1H, dd, J+7.4, 6.0 Hz), 3.87 (1H, ddd, J=7.8, 7.4, 4.6 Hz), 2.47 (1H, dtd, J=17.3, 5.4, 4.6 Hz), 2.11 (1H, ddd, J=17.3, 7.8, 3.4 Hz), 1.9 (1H, br ss), 1.46 (3H, s), 1.38 (3H, s); $^{13}$C NMR (CDCl$_3$ $\delta$ 129.3 (CH, 125.3 (C), 110.1 (C), 78.8 (CH), 75.7 (CH, 67.8 (CH), 30.7 (CH$_2$), 28.0 (CH$_3$), 26.1 (CH$_3$), 26.1 (CH$_3$), MS (Cl) m/z (rel. intensity) 189 (M$^+$-16, 75), 129 (100), 101 (20), 59 (50); Anal. Calcd for C$_9$H$_{13}$O$_3$Cl: C, 52.82; H, 6.40; Found: C, 52.92; H, 6.42.

(1S,2S,3R)-6-Bromo-3-hydroxy-1,2-O-isopropylidene cyclohex-5-ene 51b

Bromoepoxide 2b (202 mg, 0.818 mmol) was dissolved in Et$_2$O (2 mL) and added to a solution of LiAlH$_4$ (31 mg, 0.818 mmol) in Et$_2$O (6 mL). The mixture was refluxed for 5 h, ethyl acetate (3 mL) was added, then 10% NaOH solution (5 mL) was added. Organic layer was washed with H$_2$O (5 mL), brine (5 mL), and dried with Na$_2$SO$_4$. Solvent was evaporated to yield 202 mg of the bromoalcohol 51b (0.81 mmol, 99% yield). A pure sample was obtained by flash chromatography (silica gel; hexane-ethyl acetate, 5.5:4.5). R$_f$=0.3 (hexane-ethyl acetate, 3:2); mp=68°-69° C. (recrystallized from CH$_2$Cl$_2$-hexane); $[\alpha]^{20}_D$= −31° (c 1.4, CHCl$_3$); IR (KBr) $\upsilon$ 3422, 2987, 1649, 1071 cm$^{-1}$; $^1$H NMR (CDCl$_3$) $\delta$ 6.13 (1H, dd, J=5.6, 3.7 Hz), 4.63 (1H, d, J=5.9 Hz), 4.09 (1H, dd, J=7.2, 6.0 Hz), 3.90 (1H, td, J=7.4, 4.7 Hz), 2.45 (1H, dt, J=17.4, 4.9 Hz), 2.3 (1H, br s), 2.09 (1H, ddd, J=17.5, 7.5, 3.6 Hz), 1.47 (3H, s), 1.39 (3H, s); $^{13}$C NMR (CDCl$_3$) $\delta$ 129.4 (CH), 119.6 (C), 109.8 (C), 78.9 (CH), 77.0 (CH), 67.5 (CH), 31.9 (CH$_2$), 28.0 (CH$_3$), 26.1 (CH$_3$); MS (Cl) m/z (rel. intensity) 249 (M$^+$, 68), 233 (100), 191 (55), 175 (73), 147 (38); Anal. Calcd for C$_9$H$_{13}$O$_3$Br: C, 43.40; H, 5.26; Found: C, 43.41; H, 5.25.

(1R,2S,3R)-1-Hydroxy-2,3-O-isopropylidene-cyclohexa-4-ene 52

Bu$_3$SnH (510 mg, 1.75 mmol) was added to a mixture of AIBN (5 mg) and the vinyl bromide 51b (218.6 mg, 0.878 mmol) in dry toluene (15 mL). The reaction mixture was refluxed for 3 h. The solvent was evaporated and the residue was purified by flash chromatography (silica gel; Et$_2$O-hexane, 7:3) to afford 119.5 mg (0.702 mmol, 80% yield) of pure 52. R$_f$=0.4 (hexane-ethyl acetate, 1:1); $[\alpha]^{28}_D$= −158° (c 2.9, CHCl$_3$); IR (neat) $\upsilon$ 3440, 2900, 1215, 1055 cm$^{-1}$; $^1$H NMR (CDCl$_3$) $\delta$ 588 (2H, m), 4.61 (1H, dd, J=6.2, 2.6 Hz), 3.97 (1H, dd, J=8.5, 6.3 Hz), 3.77 (1H, ddd, J=8.8, 5.1 Hz), 2.50 (1H, br s), 2.41 (1H, ddd, J=17.4, 5.1, 4.5) Hz, 2.03 (1H, ddd, J=17.8, 9.8, 1.6 Hz), 1.49 (3H, s), 1.39 (3H, s); $^{13}$C NMR (CDCl$_3$) $\delta$ 129.3 (CH), 124.2 (CH), 109.1 (C), 79.4 (CH, 72.7 (CH), 69.2 (CH), 30.7 (CH$_2$), 28.3 (CH$_3$), 25.8 (CH$_3$); MS (EI, 70 eV) m/z (rel. intensity) 170 (M$^+$, 2), 155 (50), 95 (100); Anal. Calcd for C$_9$H$_{14}$O$_3$: C, 63.51; H, 8.29; Found: C, 63,41; H, 8.33.

(1R,2S,3R)-1,2,3-Triol-4-cyclohexane 53

Acetonide 52 (32.5 mg, 0.19 mmol) was dissolved in a mixture of AcOH/THR/H$_2$O (2:1:1, 3 mL). The solution was stirred at 60° C. for 4 h, the solvent was evaporated to give 24.7 mg (0.19 mmol, 100% yield) of the triol 53. An analytical sample was obtained after recrystallization from MeOH—Et$_2$O. R$_f$=0.36 (CHCl$_3$/MeOH, 4:1); mp=130° C.; $[\alpha]^{25}_D$= −194° (c 0.3, MeOH); IR (neat) $\upsilon$ 3209, 3039, 1648, 1101 cm$^{-1}$; $^1$H NMR (D$_2$O) $\delta$ 5.64 (1H, ddd, J=10, 4.4, 2.3 Hz), 5.57 (1H, ddd, J=10, 4.1, 2.3 Hz), 4.09 (1H, dd, J=4.0, 4.0 Hz), 3.74 (1H, ddd, J=8.5, 8.5, 2.0 Hz), 3.49 (1H, dd, J=9.5, 4.3 Hz), 2.37 (1H, ddd, J=17.7, 5.7, 4 Hz), 1.87 (1H, ddd, J=17.7, 8.5, 4.0 Hz); $^{13}$C NMR (D$_2$O) $\delta$ 126.7 (CH), 123.9 (CH), 70.7 (CH), 64.6 (CH), 64.5 (CH), 30.5 (CH$_2$); MS (EI, 70 eV) m/z (rel. intensity) 113 (M$^+$-17, 100), 95 (30); Anal. Calcd for C$_6$H$_{10}$O$_3$: C, 55.37; H, 7.74; Found: C, 55.26; H, 7.72.

What is claimed:

1. A method for the stereoselective production of a cyclitol, said method comprising:

a) providing an arene diol of the formula:

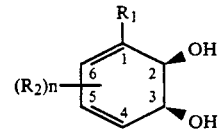

wherein R$_1$ is halogen, lower alkyl or lower alkenyl; R$_2$ is halogen or hydrogen; and n is 0–3; and b) protecting such diol as a chiral diol by adding a catalytic amount of acid in an appropriate solvent with stirring at room temperature, to allow for face selectivity in subsequent hydroxylation or oxygenation methods, said protected diol having the formula:

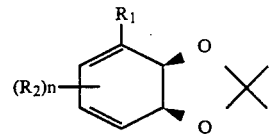

2. A method for producing a triol useful as an intermediate, said triol having the formula:

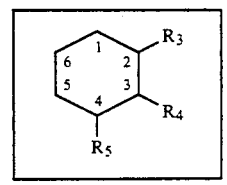

wherein R3, R4 and R5 are hydroxyl or a primary, secondary or tertiary alcohol, said method comprising:

a) providing a substituted arene diol of formula;

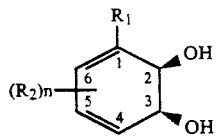

wherein R$_1$ is halogen, lower alkyl or lower alkenyl; R$_2$ is halogen or hydrogen, and n is 0 to 3;

b) protecting the diol functionality of said substituted arene diol by adding a catalytic amount of acid in an appropriate solvent, with stirring, at room temperature, to allow for face selectivity in subsequent oxygenation or hydroxylation of the diol;

c) subjecting such protected substituted diol to epoxidation in the presence of peroxy acid to yield an epoxide between carbons 4 and 5 of said diol;

d) treating said epoxide with hydride reagent such as LiAlH$_4$ in an appropriate solvent to provide a compound of the formula;

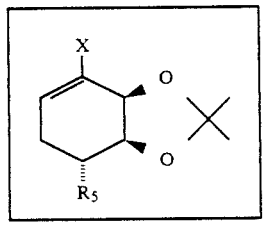

wherein X is Cl or Br and R$_5$ is as defined above; and e) reducing the functionality at carbon 1 to hydrogen by reacting the compound of step d) with a reducing agent such as tributyltin hydride alone or in combination with a radical initiator such as AIBN; and f) hydrolyzing the product of step (e) with acid to deprotect the stereocontrolling protecting group at C2–C3.

3. A method of claim 2 wherein R$_1$ is Cl or Br.

4. A method for producing a triol useful as an intermediate, said triol having the formula:

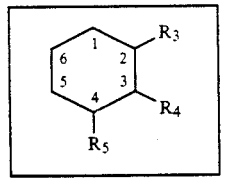

wherein R3, R4 and R5 are hydroxyl or a primary, secondary or tertiary alcohol, said method comprising:

a) providing a substituted arene diol of formula

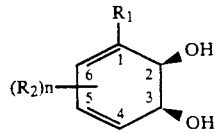

wherein R$_1$ is halogen, lower alkyl; R$_2$ is halogen or hydrogen, and n is 0 to 3;

b) protecting the diol functionality of said substituted arene diol by adding a catalytic amount of acid in an appropriate solvent, with stirring, at room temperature, to allow for face selectivity in subsequent oxygenation or hydroxylation of said diol;

c) forming an endoperoxide between carbons 1 and 4 of said protected substituted diol by treating the compound of step b) dissolved in an appropriate solvent such as carbontetrachloride, with singlet oxygen at a temperature of about 20° C.;

d) treating said endoperoxide with thiourea in an appropriate solvent such as methanol at about 10° C. to provide a compound of the formula

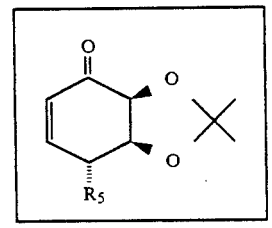

wherein R$_5$ is defined above; and e) hydrolyzing the product of step (d) with acid to deprotect the stereocontrolling protecting group at C2–C3.

5. A method of claim 4 wherein R$_1$ is Cl or Br.

6. A method for producing a tetrol useful as an intermediate, said tetrol having the formula:

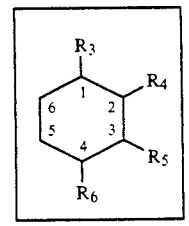

wherein R3, R4, R5 and R6 are hydroxyl or a primary, secondary or tertiary alcohol, said method comprising:

a) providing a substituted arene diol of formula

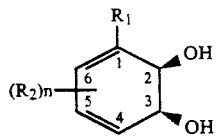

wherein R1 is halogen, lower alkyl or lower alkenyl; R2 is halogen or hydrogen; and n is 0 to 3;

b) protecting the diol functionality of said substituted arene diol by adding a catalytic amount of acid in an appropriate solvent, with stirring, at room temperature, to allow for face selectivity in subsequent oxygenation or hydroxylation of said diol;

c) forming an endoperoxide between carbons 1 and 4 of said protected substituted diol by treating the compound of step b), dissolved in an appropriate solvent such as carbontetrachloride, with singlet oxygen at a temperature of about 20° C.;

d) treating said endoperoxide with thiourea in an appropriate solvent such as methanol at about 10° C. to form an enone of the formula:

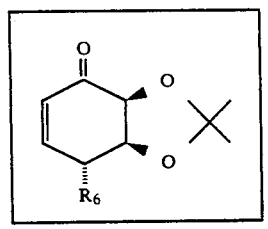

wherein $R_6$ is as defined above;

e) protecting $R_6$ with a protecting group such as t-butyldimethylchlorosilane added in an appropriate solvent at room temperature;

f) reducing the functionality at carbon 1 of said enone to OH by adding to a solution of ketone from step e) an appropriate reducing agent such as L-selectride in an appropriate solvent at a temperature of about 0° C;

g) hydrolyzing the product of step (f) with acid to deprotect the stereocontrolling protection group at C2–C3.

7. A method of claim 6 wherein $R_1$ = Cl or Br.

8. A method of producing a tetrol useful as an intermediate, said tetrol having the formula:

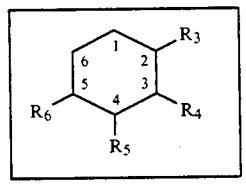

wherein $R_3$, $R_4$, $R_5$ and $R_6$ are hydroxyl or a primary, secondary or tertiary alcohol, said method comprising:

a) providing a substituted arene diol of formula

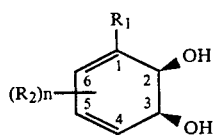

wherein $R_1$ is halogen, lower alkyl or lower alkenyl; $R_2$ is halogen or hydrogen; and n is 0 to 3;

b) protecting the diol functionality of said substituted arene diol by adding a catalytic amount of acid in an appropriate solvent, with stirring, at room temperature, to allow for face selectivity in subsequent oxygenation or hydroxylation of said diol;

c) subjecting said protected substituted diol to epoxidation in the presence of peroxy acid to form an epoxide between carbons 4 and 5 of said diol;

d) treating the product of step (c) with acidified water or an appropriate acidified alcohol to produce a compound of the formula:

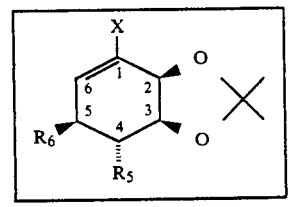

wherein X is Cl or Br and $R_5$ and $R_6$ are as defined above;

e) reducing the functionality at carbon 1 to hydrogen by contacting the compound of step d) with a reducing agent such as tributyltin hydride alone or in combination with a radical initiator such as AIBN; and f) hydrolyzing the product from step (e) with acid to deprotect the stereocontrolling protecting group at C2–C3.

9. A method of claim 8 wherein $R_1$ is Cl or Br.

10. A method of producing a tetrol of formula:

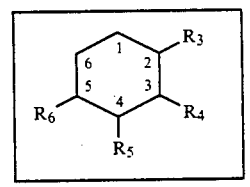

wherein $R_3$, $R_4$, $R_5$ and $R_6$ are hydroxyl or a primary, secondary or tertiary alcohol, said method comprising:

a) subjecting a compound of the formula

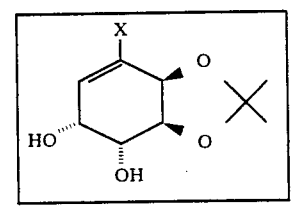

(where X = Cl or Br)
to reduction with LiAlH$_4$ in the presence of THF at room temperature to yield the compound of the formula:

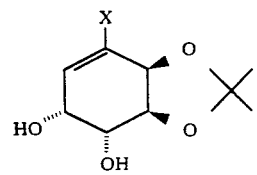

b) hydrolyzing the product of step (a) with acid to deprotect the stereocontrolling protecting group at C2–C3.

11. A method of producing a tetrol of the formula

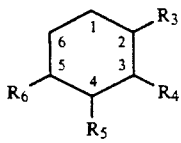

wherein R₃, R₄, R₅ and R₆ are hydroxyl or a primary, secondary or tertiary alcohol, said method comprising:
a) subjecting a compound of the formula

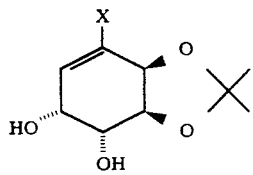

(where X=Cl or Br)
to tributyltin hydride in the presence of AIBN in Toluene to yield a compound of the formula:

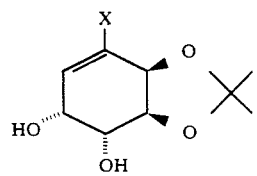

and
b) treating the product of step (a) with acid to deprotect the stereocontrolling protecting group at C2-C3.

12. A method of producing a tetrol of formula:

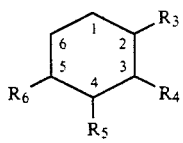

wherein R3, R4, R5 and R6 are hydroxyl or a primary, secondary or tertiary alcohol, said method comprising the steps of:
a) providing a substituted arene diol of formula

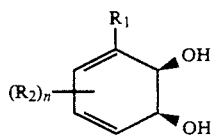

wherein R1 is halogen, lower alkyl or lower alkenyl, R2 is halogen or hydrogen; and n is 0 to 3;
b) protecting the diol functionality of said substituted arene diol by adding a catalytic amount of acid in an appropriate solvent, with stirring, at room temperature, to allow for face selectivity in subsequent oxygenation or hydroxylation of said diol;
c) forming an epoxide between carbons 4 and 5 of said protected substituted arene diol by adding to the compound of step b) peroxy acid;

d) treating said epoxide with acidified water or an appropriate acidified alcohol at room temperature to provide a compound of the formula:

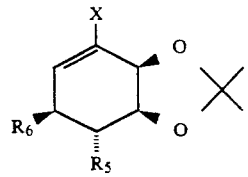

wherein X is Cl or Br and, R₅ and R₆ are as defined above;
e) reducing the functionality at carbon 1 to hydrogen by adding an appropriate reducing agent such as LiAlH₄ in an appropriate solvent such as anhydrous tetrahydrofuran with stirring at room temperature; and
f) treating the product of step (e) with acid to deprotect the stereocontrolling protection group at C2-C3.

13. A method of claim 12 wherein R₁=Cl or Br.

14. A method of producing Conduritol A, said method comprising the steps of:
a) treating (2R,3S)-2,3-O-isopropylidene-1-chlorocyclohexa-4,6-diene, AA with singlet oxygen to produce (1S,2S,3S,4R)-1-chloro-2,3-O-isopropylidene-5,6-dioxabicyclo[2.2.2]octa-7-ene, 21;
b) treating the product of step (a) with thiourea to produce (2S,3S,4R)-4-hydroxy-2,3-O-isopropylidene cyclohex-5-enone, 8;
c) treating the product of step (b) with t-butyldimethyl chlorosilane to produce (4R,5S,6R)-4-O-(t-butyldimethylsilyl)-5,6-di-O-isopropylidene/cyclohex-2-en-1-one, 28;
d) treating the product of step (c) with NaBH₄ to produce (1S,2R,3S,4R)-2,3-O-isopropylidene-1,4-dihydroxycyclohex-5-ene, 30; and
e) deprotecting the product of step (d) with aqueous acetic acid to produce Conduritol A.

15. A method of producing Conduritol A, said method comprising the steps of:
a) treating (2R,3S)-2,3-O-isopropylidene-1-chlorocyclohexa-4,6-diene, AA with singlet oxygen to produce (1S,2S,3S,4R)-1-chloro-2,3-O-isopropylidene-5,6-dioxabicyclo[2.2.2]octa-7-ene, 21;
b) reducing the product of step (a) with Al/Hg to produce (1S,2R,3S,4R)-2,3-O-isopropylidene-1,4-dihydroxycyclohex-5-ene, 30; and
c) deprotecting the product of step (b) with aqueous acetic acid to produce Conduritol A.

16. A method of producing Conduritol C, said method comprising the steps of:
a) treating (2R,3S)-2,3-O-isopropylidene-1-chlorocyclohexa-4,6-diene AA with singlet oxygen at a temperature of about 20° C. to produce (1S,2S,3S,4R)-1-chloro-2,3-O-isopropylidene-5,6-dioxabicyclo[2.2.2]octa-7-ene 21;
b) treating the product of step (a) with thiourea to produce (2S,3S,4R)-4-hydroxy-2,3-O-isopropylidene cyclohex-5-enone 8;
c) treating the product of step (b) with t-butyldimethylchlorosilane at room temperature to produce (4R,5S,6R)-4-O-(t-butyldimethylsilyl)-5,6-di-O-isopropylidene/cyclohex-2-en-1-one, 28;
d) treating the product of step (c) with L-selectride at room temperature to produce (1R,2R,3R,4R)-1- hydroxy-2,3-di-O-(isopropylidene-4-O-(t-butyl-dimethylsilyl)-cyclohex-5-ene, 29; and e) treating at room temperature, the product of step (d) with aqueous acetic acid to produce Conduritol C.

17. A method of producing Dihydroconduritol C, said method comprising the steps of:
   a) treating (2R,3S)-2,3-O-isopropylidene-1-chlorocyclohexa-4,6-diene AA with singlet oxygen at a temperature of about 20° C. to produce (1S,2S,3S,4R)-1-chloro-2,3-O-isopropylidene-5,6-dioxabicyclo[2.2.2]octa-7-ene 21;
   b) treating the product of step (a) with thiourea to produce (2S,3S,4R)-4-hydroxy-2,3-O-isopropylidene cyclohex-5-enone 8;
   c) treating the product of step (b) by hydrogenation to produce (2S,3S,4R)-4-O-(t-Butyldimethysilyl)-2,3-di-O-isopropylidenecyclohexan-1-one, 27;
   d) treating the product of step (c) with L-selectride in THF at a temperature of about 0° C. to yield (1R,2R,3R,4R)-1-Hydroxy-2,3-di-O-isopropylidene-4-O-(t-butyldimethylsilyl)cyclohexane, 33; and
   e) treating the product of step (d) with hydrochloric acid in the presence of an acetone-water mixture to produce (−)-Dihydroconduritol C.

18. A method to produce Conduritol E, said method comprising the steps of:
   a) treating (2R, 3S)-2,3-O-isopropylidene-1-bromocyclohexa-4,6-diene, D with osmium tetroxide to produce (1R,2R,3S,4S)-5-bromo-1,2-dihydroxy-3,4-di-O-isopropylidene-cyclohex-5-ene, 3b;
   b) reducing the product of step (a) in the presence of LiAlH$_4$ or Bu$_3$SnH to produce (1R,2R,3S,4R)-1,2-Dihydroxy-3,4-di-O-isopropylidenecyclohex-5-ene 14; and
   c) deprotecting the product of step (b) by treating with aqueous acetic acid to produce Conduritol E.

19. A method of producing Conduritol F, said method comprising the steps of:
   a) treating (2R, 3S)-2,3-O-isopropylidene-1-bromocyclohexa-4,6-diene D with m-chloroperbenzoic acid to produce (1R, 4S, 5S, 6R)-3-bromo-4,5-di-O-isopropylidene-7-oxa-bicyclo[4.1.0]hept-2-ene, 2a;
   b) treating the product of step (a) with aqueous base to produce (1S,2R,3S,4S)-5-bromo-1,2-dihydroxy-3,4-di-O-isopropylidene cyclohex-5-ene, 15;
   c) reducing the product of step (b) in the presence of Bu$_3$SnH to produce (1S,2R,3R,4R)-1,2-Dihydroxy-3,4-di-O-isopropylidene cyclohex-5-ene, 31; and
   d) deprotecting the product of step (c) by treating with aqueous acetic acid to produce Conduritol F.

20. A method of producing (−)-Pinitol, said method comprising the steps of:
   a) treating (2R, 3S)-2,3-O-isopropylidene-1-chlorocyclohexa-4,6-diene AA with n-chloroperbenzoic acid to produce (1R, 4S, 5S, 6R)-3-chloro-4,5-di-O-isopropylidene-7-oxabicyclo[4.1.0]hept-2-ene, 2a;
   b) treating the product of step (a) with acidified methanol to produce (3R,4R,5S,6S)-1-Chloro-4-hydroxy-5,6-di-O-isopropylidene-3-O-methylcyclohex-1-ene, 24a;
   c) reducing the product of step (b) in the presence of LiAlH$_4$ to produce (3R,4R,5S,6S)-3-O-methyl-4-hydroxy-5,6-di-O-isopropylidene cyclohex-1-ene, 25;
   d) treating the product of step (c) with osmium tetroxide to produce (1S,2S,3S,4R,5S,6R)-2,3,6-Trihydroxy-4,5-di-O-isopropylidene-1-O-methylcyclohexane, 26; and
   e) deprotecting the product of step (d) in aqueous acetic acid to produce (−)-Pinitol.

21. A method of producing (−)-Pinitol, said method comprising the steps of:
   a) treating (2R,3S)-2,3-O-isopropylidene-1-bromocyclohexa-4,6-diene, D, with m-chloroperbenzoic acid to produce (1R,4S,5S,6R)-3-bromo-4,5-di-O-isopropylidene-7-oxa-bicyclo[4.1.0]hept-2-ene, 2b;
   b) treating the product of step (a) with acidified methanol to produce (3R,4R,5S,6S)-1-bromo-4-hydroxy-5,6-di-O-isopropylidene-3-O-methylcyclohex-1-ene,24b;
   c) reducing the product of step (b) in the presence of LiAlH$_4$ to produce (3R,4R,5S,6S)-3-O-methyl-4-hydroxy-5,6-di-O-isopropylidenecyclohex-1-ene;25;
   d) treating the product of step (c) with osmium tetraoxide to produce (1S,2S,3S,4R,5S,6R)-2,3,6-Trihydroxy-4,5-di-O-isopropylidene-1-O-methylcyclohexane,26; and
   e) deprotecting the product of step (d) in aqueous acetic acid to produce (−)-Pinitol.

22. A method of producing (+)-Pinitol, said method comprising the steps of:
   a) treating (2R,3S)-2,3-O-isopropylidene-1-bromocyclohexa-4,6-diene, D with osmium tetroxide to produce (1R,2R,3S,4S)-5-bromo-1,2-dihydroxy-3,4-di-O-isopropylidene-cyclohex-5-ene, 3b;
   b) reducing the product of step (a) in the presence of LiAlH$_4$ or Bu$_3$SuH to produce (1R,2R,3S,4R)-1,2-Dihydroxy-3,4-di-O-isopropylidene cyclohex-5-ene,14;
   c) treating the product of step (b) with m-chloroperbenzoic acid to produce an epoxide (1S,2R,3R,4S,5R,6S)-2,3-Dihydroxy-4,5-di-O-isopropylidene-7-oxa-bicyclo[4.1.0]heptane,22;
   d) treating the product of step (c) with methanol and neutral alumina to produce (1R,2R,3R,4S,5R,6S)-2,3,6-Trihydroxy-4,5-di-O-isopropylidene-1-O-methylcyclohexane,23; and e) deprotecting the product of step (d) with aqueous acetic acid to produce (+)-Pinitol.

23. A method of producing D-chiroinositol, said method comprising the steps of:
   a) treating (2R,3S)-2,3-O-isopropylidene-1-bromocyclohexa-4,6-diene, D with osmium tetroxide to produce (1R,2R,3S,4S)-5-bromo-1,2-dihydroxy-3,4-di-O-isopropylidene-cyclohex-5-ene, 3b;
   b) treating (2R,3S)-2,3-O-isopropylidene-1-bromocyclohexa-4,6-diene, D with osmium tetroxide to produce (1R,2R,3S,4S)-5-bromo-1,2-dihydroxy-3,4-di-O-isopropylidene-cyclohex-5-ene, 3b;
   c) subjecting the product of step (b) to hydrolysis with H$_3$O$^+$; and
   d) deprotecting the product of step (c) with aqueous acetic acid to produce D-chiroinositol.

24. A method of producing (1R,2S,3R)-1,2,3-Triol-4-cyclohexane,53, useful as a chiral synthon, said method comprising the steps of:
   a) treating (2R,3S)-2,3-O-isopropylidene-1-chlorocyclohexa-4,6-diene AA with m-chloroperbenzoic acid to produce (1R,4S,5S,6R)-3-chloro-4,5-di-O-isopropylidene-7-oxabicyclo[4.1.0]hept-2-ene, 2a;

b) reducing the product of step (a) in the presence of LiAlH₄ to produce (1S,2S,3R)-6-chloro-3-hydroxy-1,2-O-isopropylidene cyclohex-5-ene,51a;

c) reducing the product of step (b) with Bu₃SnH to produce (1R,2S,3R)-1-hydroxy-2,3-O-isopropylidene-cyclohexa-4-ene,52; and d) deprotecting the product of step (c) with aqueous acetic acid to produce (1R,2S,3R)-1,2,3-triol-4-cyclohexane,53.

25. A method of producing (1R,2S,3R)-1,2,3-triol-4-cyclohexane,53, useful as a chiral synthon, said method comprising the steps of:

a) treating (2R,3S)-2,3-O-isopropylidene-1-bromocyclohexa-4,6-diene, D, with m-chloroperbenzoic acid to produce (1R,4S,5S,6R)-3-bromo-4,5-di-O-isopropylidene-7-oxa-bicyclo[4.1.0]hept-2-ene,2b;

b) reducing the product of step (a) in the presence of LiAlH₄ to produce (1S,2S,3R)-6-bromo-3-hydroxy-1,2-O-isopropylidene cyclohex-5-ene,51b;

c) reducing the product of step (b) with Bu₃SnH to produce (1R,2S,3R)-1-hydroxy-2,3-O-isopropylidene-cyclohexa-4-ene,52; and d) deprotecting the product of step (c) with aqueous acetic acid to produce (1R,2S,3R)-1,2,3-trio-4-cyclohexane,53.

26. An intermediate compound useful in the synthesis of cyclitols, said intermediate being selected from the group consisting of:

(1S,2R,3R,4R)-1,2-Dihydroxy-3,4-di-O-isopropylidene cyclohex-5-ene; (1R,2R,3S,4R)-1,2-dihydroxy-3,4-di-O-isopropylidene cyclohex-5-ene; (1S,2R,3R,4S,5R,6S)-2,3-Dihydroxy-4,5-di-O-isopropylidene-7-oxa-bicyclo[4.1.0]heptane; (1R,2R,3R,4S,5R,6S)-2,3,6-trihydroxy-4,5-di-O-isopropylidene-1-O-methylcyclohexane; (3R,4R,5S,6S)-1-Chloro-4-hydroxy-5,6-di-O-isopropylidene-3-O-methylcyclohex-1-ene; (3R,4R,5S,6S)-1-Bromo-4-hydroxy-5,6-di-O-isopropylidene-3-O-methylcyclohex-1-ene; (3R,4R,5S,6S)-3-O-Methyl-4-hydroxy-5,6-di-O-isopropylidene cyclohex-1-ene; (4R,5S,6R)-4-O-(t-butyldimethylsilyl)-5,6-di-O-isopropylidenelcyclohex-2-en-1-one; (2S,3S,4R)-4-O-(t-butyldimethylsilyl)-2,3-di-O-isopropylidenecyclohexan-1-one; (1R,2R,3R,4R)-1-hydroxy-2,3-di-O-isopropylidene-4-O-(t-butyldimethylsilyl)cyclohexane; (1R,2R,3R,4R)-1-Hydroxy-2,3-di-O-isopropylidene-4-O-(t-butyldimethylsilyl)cyclohex-5-ene; (1S,2R,3S,4R)-2,3-O-isopropylidene-1,4-dihydroxycyclohex-5-ene; (1S,2S,3R)-6-Chloro-3-hydroxy-1,2-O-isopropylidene cyclohex-5-ene; (1S,2S,3R)-6-Bromo-3-hydroxy-1,2-O-isopropylidene cyclohex-5-ene; (1R,2S,3R)-1-Hydroxy-2,3-O-isopropylidene-cyclohexa-4-ene.

* * * * *